United States Patent
Li et al.

(10) Patent No.: US 9,693,554 B2
(45) Date of Patent: Jul. 4, 2017

(54) PLANT GROWTH ACCELERATOR

(71) Applicant: COSMO OIL CO., LTD., Minato-ku (KR)

(72) Inventors: Jun Li, Minato-ku (JP); Yasunobu Ueda, Satte (JP); Shigeyuki Watanabe, Satte (JP); Yasutomo Takeuchi, Utsunomiya (JP)

(73) Assignee: COSMO OIL CO., LTD., Minato-ku (JP)

( * ) Notice: Subject to any disclaimer, the term of this patent is extended or adjusted under 35 U.S.C. 154(b) by 0 days.

(21) Appl. No.: 14/773,074

(22) PCT Filed: Mar. 6, 2014

(86) PCT No.: PCT/JP2014/055743
§ 371 (c)(1),
(2) Date: Sep. 4, 2015

(87) PCT Pub. No.: WO2014/136863
PCT Pub. Date: Sep. 12, 2014

(65) Prior Publication Data
US 2016/0007599 A1    Jan. 14, 2016

(30) Foreign Application Priority Data
Mar. 7, 2013 (JP) ................ 2013-045083

(51) Int. Cl.
*A01N 33/04* (2006.01)
*A01N 37/44* (2006.01)
*A01G 7/00* (2006.01)

(52) U.S. Cl.
CPC .......... *A01N 37/44* (2013.01); *A01G 7/00* (2013.01)

(58) Field of Classification Search
None
See application file for complete search history.

(56) References Cited

U.S. PATENT DOCUMENTS 4,322,440 A * 3/1982 Fish ............... A61K 31/16
                                                   514/550
5,298,482 A    3/1994 Tanaka et al.

FOREIGN PATENT DOCUMENTS

| EP | 0 514 776 A1 | 11/1992 |
| EP | 514776 | * 11/1992 |
| EP | 07053487 | * 2/1995 |
| JP | 4-338305 A | 11/1992 |
| JP | 7-53487 A | 2/1995 |
| JP | 9-101599 A | 4/1997 |
| JP | 2002-284750 | 10/2002 |
| JP | 2003-088393 | * 3/2003 |
| JP | 2011-121878 | 6/2011 |
| JP | 2011-121878 A | 6/2011 |

OTHER PUBLICATIONS

Hotta et al.(Promotive effects of 5-aminolevulinic acid on the yield of several crops, Plant Growth Regulation 22: 109-114, 1997).*
Herdeis(Chirospecific Synthesis of (S)(+) and (R)(−)-5-amino-4-hydroxypentanoic acid, Synthesis, vol. 3, Jan. 1, 1986).*
Combined Chinese Office Action and Search Report issued Mar. 28, 2016 in Patent Application No. 201480012757.0 (with English translation of Categories of Cited Documents).
International Search Report issued Apr. 28, 2014, in PCT/JP2014/055743 filed Mar. 6, 2014.
Written Opinion of the International Searching Authority issued Apr. 28, 2014, in PCT/JP2014/055743 filed Mar. 6, 2014.
Hiroyuki Sugiura, Effects of Ethephon and Gibberellin Applications on Growth of Taranoki (*Aralia elate Seem.*), Japanese Journal Pesticide Science, vol. 30, No. 2, 153-156, 2005, (with English Abstract).
Zaochang Liu et al, "Effects of Foliar and Root-Applied Benzylaminopurine on Tillering of Rice Plants Grown in Hydroponics" and Chunsheng Mu et al, "Effects of Gibberellic Acid Application on Panicle Characteristics and Size of Shoot Apex in the First Bract Differentiation Stage in Rice", Japanese Journal of Crop Science, vol. 70, No. 3, p. 471, 2001, (Total—11 pages).
John Lokvam et al., Allelochemical Function for a Primary Metabolite: The Case of L-Tyrosine Hyper-Production in *Inga umbellifera* (Febaceae)[1], American Journal of Botany, 2006, vol. 93, No. 8, p. 1109-1115.
Masana Noma et al., "Isolation and Characterization of Hydroxyvaleric Acid Derivatives from Tobacco Leaves and the Hydrolyzate of Tobacco Extract", Agricultural and Biological Chemistry, 1977, vol. 41, No. 5, p. 913-915.
Extended Search Report issued Jul. 21, 2016 in European Patent Application No. 14759651.4.
C.Herdeis, "Chirospecific Synthesis of (S)-(+)- and (R)-(−)-5-Amino-4-hydroxypentanoic Acid from L- and D-Glutamic Acid via (S)-(+)- and (R)-(−)-5-Hydroxy-2-oxopiperidine", Synthesis, vol. 3, Jan. 1, 1986, XP055287184, 2 pages.
Y. Hotta, et al., "Promotive effects of 5-aminolevulinic acid on the yield of several crops", Plant Growth Regulation, vol. 22, No. 2, 1997, XP-001118762, pp. 109-114.

* cited by examiner

*Primary Examiner* — Alton Pryor
(74) *Attorney, Agent, or Firm* — Oblon, McClelland, Maier & Neustadt, L.L.P.

(57) ABSTRACT

Plant growth accelerator comprising, as an active ingredient, 5-amino-4-hydroxypentanoic acid of formula (1)

$$H_2NCH_2CH(OH)CH_2CH_2COOR^1 \qquad (1)$$

wherein $R^1$ represents a hydrogen atom or a hydrocarbon group having 1 to 10 carbon atoms, a derivative thereof or a salt thereof.

8 Claims, No Drawings

PLANT GROWTH ACCELERATOR

TECHNICAL FIELD

The present invention relates to a novel plant growth accelerator.

BACKGROUND ART

In recent years, the worldwide continuous population growth together with the changing food supply/demand mapping are causing concerns on the food shortage at a faster pace. Under the circumstances, one of the countermeasures is considered to improve labor saving and operational efficiency and enhance the productivity in agriculture.

Cultivation techniques, equipment and chemical agents have been studied for a very long time for the purpose of improving labor saving and operational efficiency, and chemical agents, among them, are expected to have a growing future demand due to a small investment for use.

Chemical agents used for the purpose of growing a plant, controlling the growth and saving labor in cultivation practice are called plant growth regulators and provide a wide variety of actions such as growth acceleration, germination inhibition, extension inhibition, induction of seedlessness and fall prevention of fruits, and the like. However, those having growth accelerating action are limited to plant hormones such as gibberellin and synthetic cytokinin and their related substances (Non Patent Literatures 1 and 2).

Period, concentration and amount applicable to these plant hormone-based plant growth regulators are limited to narrow ranges since their actions are significantly affected by the variations thereof. When used under wrong application conditions, these regulators not only fail to provide the expected effects but also fail to exhibit healthy growth, and thus they are not commonly used.

Meanwhile, some amino acid-based compounds are reported to promote plant growth, for example, glutamic acid, glycine, proline, and the like. 5-aminolevulinic acid also has actions such as photosynthesis activity enhancement and nitrogen absorption promotion. These amino acid-based compounds have mild actions and hence have wide ranges of period, concentration and amount which can be applied. For this reason, they are expected to be easy-to-use chemical agents and consequently further development is demanded.

Among the amino acid-based compounds, 5-amino-4-hydroxy pentanoic acid and derivatives thereof are known to have been used as the production intermediate for pharmaceutical products (Patent Literatures 1 and 2) but the actions thereof on plants are not known at all.

CITATION LIST

Patent Literature
Patent Literature 1
   JP-A-2002-284750
Patent Literature 2
   JP-A-2003-88393
Non Patent Literature
Non Patent Literature 1
   Japanese Journal Pesticide Science, Vol. 30, No. 2, 153-156, 2005
Non Patent Literature 2
   Japanese Journal of Crop Science, Vol. 70, No. 3, 471, 2001

SUMMARY OF INVENTION

Consequently, it is an object of the present invention to provide a novel plant growth accelerator having an amino acid compound as an active ingredient.

Under the circumstances, the present inventors have conducted extensive studies and found that the growth of a plant can be accelerated when 5-amino-4-hydroxypentanoic acid, a derivative thereof or a salt thereof is applied to the plant, whereby the present invention has been accomplished.

More specifically, the present invention provides a plant growth accelerator comprising, as an active ingredient, 5-amino-4-hydroxypentanoic acid of formula (1)

$$H_2NCH_2CH(OH)CH_2CH_2COOR^1 \qquad (1)$$

wherein $R^1$ represents a hydrogen atom or a hydrocarbon group having 1 to 10 carbon atoms, a derivative thereof or a salt thereof.

Further, the present invention provides a method for accelerating plant growth which uses 5-amino-4-hydroxypentanoic acid represented by the above formula (1), a derivative thereof or a salt thereof.

Advantageous Effect of Invention

According to the present invention, the growth of a plant can be accelerated and the cultivation period can be shortened. Thus, according to the present invention, the plant cultivation can be labor-saving and operationally efficient.

DESCRIPTION OF EMBODIMENTS

The active ingredient of the plant growth accelerator of the present invention is 5-amino-4-hydroxypentanoic acid, a derivative thereof (the above formula (1)) or a salt thereof.

In the formula (1), $R^1$ represents a hydrogen atom or a hydrocarbon group having 1 to 10 carbon atoms. The hydrocarbon group has preferably 1 to 6 carbon atoms.

Examples of the hydrocarbon group $R^1$ include saturated aliphatic hydrocarbon groups having 1 to 10 carbon atoms, unsaturated aliphatic hydrocarbon groups having 2 to 10 carbon atoms, alicyclic hydrocarbon groups having 3 to 10 carbon atoms, alicyclic-aliphatic hydrocarbon groups having 4 to 10 carbon atoms, aromatic hydrocarbon groups having 6 to 10 carbon atoms and aromatic-aliphatic hydrocarbon groups having 7 to 10 carbon atoms. Preferable hydrocarbon group includes saturated aliphatic hydrocarbon groups.

Examples of the above saturated aliphatic hydrocarbon group include methyl, ethyl, n-propyl, isopropyl, n-butyl, isobutyl, tert-butyl, n-pentyl, isopentyl, neopentyl, tert-pentyl, 2-methylbutyl, n-hexyl, isohexyl, 3-methylpentyl, ethylbutyl, n-heptyl, 2-methylhexyl, n-octyl, isooctyl, tert-octyl, 2-ethylhexyl, 3-methyl heptyl, n-nonyl, isononyl, 1-methyloctyl, ethylheptyl, n-decyl and 1-methylnonyl, and preferable saturated aliphatic hydrocarbon groups include linear or branched chain alkyl groups having 1 to 6 carbon atoms such as methyl, ethyl, n-propyl, isopropyl, n-butyl, isobutyl, tert-butyl, n-pentyl and n-hexyl.

Specific examples of the above unsaturated aliphatic hydrocarbon group suitably include vinyl, allyl, isopropenyl, 2-butenyl, 2-methylallyl, 1,1-dimethylallyl, 3-methyl-2-butenyl, 3-methyl-3-butenyl, 4-pentenyl, n-hexenyl, n-octenyl, n-nonenyl and n-decenyl, and preferable unsaturated aliphatic hydrocarbon groups include linear or branched chain alkenyl groups having 2 to 6 carbon atoms such as vinyl, allyl, isopropenyl, 2-butenyl, 2-methylallyl, 1,1-dimethylallyl, 3-methyl-2-butenyl, 3-methyl-3-butenyl, 4-pentenyl and n-hexenyl.

Specific examples of the above alicyclic hydrocarbon group suitably include cyclopropyl, cyclobutyl, cyclopentyl, cyclohexyl, cycloheptyl, cyclooctyl, 3-methylcyclohexyl, 4-methylcyclohexyl, 4-ethylcyclohexyl, 2-methylcyclooctyl, cyclopropenyl, cyclobutenyl, cyclopentenyl, cyclohexenyl, cyclopentenyl, cyclooctenyl, 4-methyl cyclohexenyl and 4-ethylcyclohexenyl, and preferable alicyclic hydrocarbon groups include cycloalkyl or cycloalkenyl groups having 3 to 6 carbon atoms such as cyclopropyl, cyclobutyl, cyclopentyl, cyclohexyl, cyclopropenyl, cyclobutenyl, cyclopentenyl and cyclohexenyl.

Specific examples of the above alicyclic-aliphatic hydrocarbon group suitably include cyclopropylethyl, cyclobutylethyl, cyclopentylethyl, cyclohexylmethyl, cyclohexylethyl, cycloheptylmethyl, cyclooctylethyl, 3-methylcyclohexylpropyl, 4-methylcyclohexylethyl,4-ethylcyclohexylethyl, cyclopropenylbutyl, cyclobutenylethyl, cyclopentenylethyl, cyclohexenylmethyl, cycloheptenylmethyl, cyclooctenylethyl and 4-methylcyclohexenylpropyl, and preferable alicyclic-aliphatic hydrocarbon group include cycloalkyl-alkyl groups having 4 to 6 carbon atoms such as cyclopropylethyl and cyclobutylethyl.

Specific examples of the above aromatic hydrocarbon group suitably include aryl groups such as phenyl and naphthyl; alkyl substituted phenyl groups such as 4-methylphenyl, 3,4-dimethylphenyl, 3,4,5-trimethylphenyl, 2-ethylphenyl, n-butylphenyl and tert-butylphenyl, and preferable aromatic hydrocarbon groups include phenyl.

Specific examples of the above aromatic-aliphatic hydrocarbon group include phenyl alkyl groups having 7 to 10 carbon atoms such as benzyl, 1-phenylethyl, 2-phenylethyl, 2-phenylpropyl, 3-phenylpropyl and 4-phenylbutyl.

Examples of the salt of the compound of formula (1) include acid addition salts such as hydrochloride, hydrobromate, hydroiodide, phosphate, methylphosphoric acid, ethylphosphoric acid, phosphite, phosphinate, nitrate, sulfate, acetate, propionate, toluenesulfonate, succinate, oxalate, lactate, tartrate, glycolate, methanesulfonate, butyrate, valerianate, citrate, fumarate, maleate and malate; metal salts such as sodium salt, potassium salt and calcium salt; ammonium salt and alkyl ammonium salt. These salts are in the form of an aqueous solution or a powder when used.

5-amino-4-hydroxypentanoic acid, derivatives thereof or salts thereof described above in detail may form a hydrate or solvate, and can be used singly or in a suitable combination of two or more. Alternatively, an optically active or racemic form thereof may be used.

5-amino-4-hydroxypentanoic acid, a derivative thereof or a salt thereof can be produced by any method of chemical synthesis, microbial production and enzymatic production, and can be produced in accordance with the method described in, for example, Patent Literature 1 or 2. 5-amino-4-hydroxypentanoic acid produced as described above, the chemical reaction solution or fermentation broth thereof before purification can be used as it is without separation or purification as long as they are free of harmful substances. Commercial products or the like can be used alternatively.

5-amino-4-hydroxypentanoic acid, a derivative thereof, or a salt thereof has an excellent plant growth accelerating action. Particularly, they are excellent in effects such as growth acceleration of plant heights, tillering acceleration and weight increase of the above-ground parts and have actions to accelerate the growth of a wide range of plants and increase crop yields.

Plants to which the plant growth accelerator of the present invention is applicable include, but not limited to, grains and vegetables, and specific examples include rice, wheat, barley, corn, buckwheat, soybean, azuki bean, peas, green soybean, beans; leaf vegetables and fruits such as tomato, eggplant, green pepper, paprika, cucumber, sweet pepper, okra, strawberry, melon, watermelon, pumpkin, gourd, cabbage, Brussels sprouts, Chinese cabbage, Komatsuna turnip green, spinach, garland chrysanthemum, potherb mustard, lettuce, parsley and Chinese chives; stem vegetables such as asparagus, green onion, onion, garlic, scallion, broccoli, cauliflower, edible chrysanthemum and Japanese ginger; root vegetable and tubers such as Japanese daikon radish, turnip, radish, carrot, lotus root, burdock, shallots, sweet potato, potato, taro and the like.

Of these, barley, Komatsuna turnip green, garland chrysanthemum, broccoli and radish are preferable.

According to the present invention, the plant growth accelerator desirably contains 5-amino-4-hydroxypentanoic acid, a derivative thereof or a salt thereof. The plant growth accelerator according to the present invention may further contain, as necessary, a plant growth modifier, a saccharide, a nitrogen containing compound, an acid, an alcohol, a vitamin, a trace element, a metal salt, a chelating agent, a preservative, an antifungal agent, or the like.

Examples of the plant growth modifier used here include brassinolides such as epibrassinolide; cholinergic agents such as choline chloride and choline nitrate; indolebutyric acid, indoleacetic acid, ethychlozate agent, 1-naphthylacetamide agent, isoprothiolane agent, nicotinamide agent, hydroxyisoxazole agent, calcium peroxide agent, benzylaminopurine agent, metasulfocarb agent, oxyethylene docosanol agent, ethephon agent, cloxyfonac agent, gibberellin, streptomycin agent, daminozide agent, benzylaminopurine agent, 4-CPA agent, ancymidol agent, inabenfide agent, uniconazole agent, chlormequat agent, dikegulac agent, mefluidide agent, calcium carbonate agent, piperonyl butoxide agent and the like.

Examples of the saccharide include glucose, sucrose, xylitol, sorbitol, galactose, xylose, mannose, arabinose, madurose, sucrose, ribose, rhamnose, fructose, maltose, lactose, maltotriose, and the like.

Examples of the nitrogen containing compound include amino acids (asparagine, glutamine, histidine, thyrosin, glycine, arginine, alanine, tryptophan, methionine, valine, proline, leucine, lysine, glutamic acid, aspartic acid and isoleucine), urea, ammonia, and the like.

Examples of the acid include organic acids (such as formic acid, acetic acid, propionic acid, butyric acid, valeric acid, oxalic acid, phthalic acid, benzoic acid, lactic acid, citric acid, tartaric acid, malonic acid, malic acid, succinic acid, glycolic acid, maleic acid, caproic acid, caprylic acid, myristic acid, stearic acid, palmitic acid, pyruvic acid, α-ketoglutaric acid and levulinic acid), sulfurous acid, sulfuric acid, nitric acid, phosphorous acid, phosphoric acid, polyphosphoric acid, and the like.

Examples of the alcohol include methanol, ethanol, propanol, butanol, pentanol, hexanol, glycerol and the like.

Examples of the vitamin include nicotinamide, vitamin $B_6$, vitamin $B_{12}$, vitamin $B_5$, vitamin C, Vitamin $B_{13}$, vitamin $B_1$, vitamin $B_3$ vitamin $B_2$, the vitamin $K_3$, vitamin A, Vitamin $D_2$, vitamin $D_3$ vitamin $K_1$, α-tocopherol, β-tocopherol, γ-tocopherol, σ-tocopherol, p-hydroxybenzoic acid, biotin, folic acid, nicotinic acid, pantothenic acid, α-lipoic acid and the like.

Examples of the trace element include boron, manganese, zinc, copper, iron, molybdenum, chlorine and the like.

Examples of the metal salt include calcium salt, potassium salt, magnesium salt and the like.

Examples of the chelating agent include aminocarboxylic acid chelating agents (ethylenediamine tetraacetic acid, nitrilotriacetic acid, hydroxyethyl iminodiacetic acid, hydroxyethyl ethylenediamine triacetic acid, diethylene triaminepentaacetic acid, triethylene tetraaminehexaacetic acid, dicarboxymethyl glutamic acid, dihydroxyethylglycine, 1,3-propanediamine tetraacetic acid, 1,3-diamino-2-hydroxypropane tetraacetic acid, and the like); and phosphonic acid chelating agents (hydroxyethylidene diphosphonic acid, methylenephosphonic acid, phosphonobutane tricarboxylic acid, and the like). These chelating agents may be used in the form of a metal salt.

The plant growth accelerator of the present invention may be applied by any method of foliage application, soil application, douche treatment or hydrodouche treatment. The growth accelerator may be absorbed to a plant before the plant is settled or a cutting is made.

When the present agent is applied by the foliage application, it is preferable that the agent contain the above 5-amino-4-hydroxypentanoic acid, a derivative thereof or a salt thereof in a concentration of from 0.0001 to 100 ppm, particularly from 0.005 to 1 ppm, and that the agent be applied in a volume of from 10 to 1000 L, particularly from 50 to 300 L per 10 are. A spreading agent can be used for a plant to whose leave surface the agent is not easily adhered such as monocotyledons, but the kind and amount thereof are not particularly limited.

When the present agent is applied by the soil application, or douche treatment or hydrodouche treatment, it is preferable that the agent contain the above 5-amino-4-hydroxypentanoic acid, a derivative thereof or a salt thereof in a concentration of from 0.0001 to 100 ppm, particularly from 0.01 to 1 ppm, and that the agent be applied in a volume of from 10 to 1000 L, particularly from 50 to 300 L, per 10 are for field grown, and from 10 ml to 2 L, particularly from 10 ml to 1 L per plant for pot grown.

When the present agent is absorbed to a plant before the plant is settled or a cutting is made, 5-amino-4-hydroxypentanoic acid, a derivative thereof or a salt thereof is absorbed by soaking, and it is desirable that the concentration of 5-amino-4-hydroxypentanoic acid, a derivative thereof or a salt thereof in a soaking liquid be from 0.00001 to 10 ppm, particularly from 0.001 to 0.1 ppm. The soaking time is desirably from 1 second to 1 week, particularly from 1 minute to 1 day.

Sufficient effects can be obtained by a single treatment but treatment of several times can further enhance the effects. In the latter case, the treatment methods described hereinbefore can also be combined.

EXAMPLES

The present invention will be described below in detail with reference to Examples which are simply for illustration, but is not limited thereto.

Example 1

Growth Accelerating Effect of 5-Amino-4-Hydroxypentanoic Acid on Barley

Barley was seeded in a pot and grown. The soil used was black soil. The plants were set at 4 plants/pot and 4 to 6 pots/area. A chemical fertilizer (containing 8% of nitrogen, phosphoric acid and potassium respectively) as a basal fertilizer was applied so that each of nitrogen, phosphoric acid and potassium was 5 kg per 10 a. 22 days after seeding, 200 L per 10 a of aqueous solutions containing 0.006 ppm, 0.06 ppm or 0.6 ppm, of 5-amino-4-hydroxypentanoic acid was applied. 35 days after seeding, the plant height, tillering and dry weight of the above-ground part were measured.

TABLE 1

|  | Areas of 5-amino-4-hydroxypentanoic acid treatment | | | Control area |
| --- | --- | --- | --- | --- |
|  | 0.006 ppm | 0.06 ppm | 0.6 ppm |  |
| Plant length (average) | 19.4 cm | 20.1 cm | 20.2 cm | 18.4 cm |
| Tillering (average) | 3.50 | 3.53 | 3.79 | 3.15 |
| Dry weight of above-ground part (average) | 103 mg | 103 mg | 112 mg | 86 mg |

As shown in Table 1, the dry weights of the above-ground part in the areas of 5-amino-4-hydroxypentanoic acid treatment had a 20 to 30% increase compared with that of the control area. This confirmed the plant growth accelerating effect.

Example 2

Growth Accelerating Effect of 5-Amino-4-Hydroxypentanoic Acid on Komatsuna Turnip Green Komatsuna turnip green was seeded and grown at a field. The soil used was red clay. The plants were set at 40 to 52 plants/section and 2 to 3 sections/area. A coated fertilizer (containing 13% nitrogen, 11% phosphoric acid and 13% potassium) as a basal fertilizer was applied so that nitrogen was 50 kg per 10 a. 22 days after seeding, 1000 L per 10 a of an aqueous solution containing 0.06 ppm of 5-amino-4-hydroxypentanoic acid was applied twice. 42 days after seeding, the fresh weight of the above-ground part was measured.

TABLE 2

|  | 5-amino-4-hydroxypentanoic acid treatment | Control area |
| --- | --- | --- |
| Fresh weight of above-ground part (average) | 40.6 g | 34.0 g |

As shown in Table 2, the fresh weight of the above-ground part in the areas of 5-amino-4-hydroxypentanoic acid treatment had a 19% increase compared with that of the control area. This confirmed the plant growth accelerating effect.

Example 3

Growth Accelerating Effect of 5-Amino-4-Hydroxypentanoic Acid on Radish

Radish was seeded in a pot and grown. The soil used was a sterilized compost containing fertilizer components (180 mg/L of nitrogen, 120 mg/L of phosphoric acid, 220 mg/L of potassium). The plants were set at 4 plants/pot and 4 pots/area. 15 days after and 21 days after seeding, 200 L per 10 a of aqueous solutions containing 0.06 ppm or 0.6 ppm of 5-amino-4-hydroxypentanoic acid was applied. 28 days after seeding, the fresh weight of the edible part was measured.

TABLE 3

| | Areas of 5-amino-4-hydroxypentanoic acid treatment | | Control area |
|---|---|---|---|
| | 0.06 ppm | 0.6 ppm | |
| Fresh weight of edible part (average) | 2.26 g | 2.54 g | 2.21 g |

As shown in Table 3, the fresh weights of the edible part in the areas of 5-amino-4-hydroxypentanoic acid treatment had a 3 to 15% increase compared with that of the control area. This confirmed the plant growth accelerating effect.

Example 4

Growth Accelerating Effect of 5-Amino-4-Hydroxypentanoic Acid on Garland Chrysanthemum Garland chrysanthemum was seeded in a pot and grown. The soil used was a sterilized compost containing fertilizer components (180 mg/L of nitrogen, 120 mg/L of phosphoric acid, 220 mg/L of potassium). The plants were set at 4 plants/pot and 4 pots/area. 4, 5, 6 and 7 weeks after seeding, 200 L per 10 a of aqueous solutions containing 0.06 ppm or 0.6 ppm of 5-amino-4-hydroxypentanoic acid was applied. 8 weeks after seeding, the fresh weight of the above-ground part was measured.

TABLE 4

| | Areas of 5-amino-4-hydroxypentanoic acid treatment | | Control area |
|---|---|---|---|
| | 0.06 ppm | 0.6 ppm | |
| Fresh weight of above-ground part (average) | 25.5 g | 24.8 g | 22.7 g |

As shown in Table 4, the fresh weights of the above-ground part in the areas of 5-amino-4-hydroxypentanoic acid treatment had a 9 to 12% increase compared with that of the control area. This confirmed the plant growth accelerating effect.

Example 5

Growth Accelerating Effect of 5-Amino-4-Hydroxypentanoic Acid on Broccoli

Commercial young plants were settled in a pot and grown. The soil used was a sterilized compost containing fertilizer components (180 mg/L of nitrogen, 120 mg/L of phosphoric acid, 220 mg/L of potassium). The plants were set at 1 plant/pot and 4 pots/area. Every week (2 weeks through 10 weeks) after settling, 200 L per 10 a of an aqueous solution containing 0.6 ppm of 5-amino-4-hydroxypentanoic acid was applied. 11 weeks after settling, the fresh weight of the edible part was measured.

TABLE 5

| | Areas of 5-amino-4-hydroxypentanoic acid treatment 0.6 ppm | Control area |
|---|---|---|
| Fresh weight of edible part (average) | 39.2 g | 36.9 g |

As shown in Table 5, the fresh weight of the edible part in the areas of 5-amino-4-hydroxypentanoic acid treatment had a 6% increase compared with that of the control area. This confirmed the plant growth accelerating effect.

The invention claimed is:

1. A method for accelerating plant growth, comprising: applying a composition comprising 5-amino-4-hydroxypentanoic acid of formula (1), or a salt thereof to a plant:

$$H_2NCH_2CH(OH)CH_2CH_2COOR^1 \qquad (1)$$

where $R^1$ represents a hydrogen atom or a hydrocarbon group having 1 to 10 carbon atoms to accelerate growth of the plant.

2. The method of claim 1, comprising applying 0.0001 ppm to 10 ppm of the 5-amino-4-hydroxypentanoic acid, or a salt thereof.

3. The method of claim 1, wherein the plant is a grain or a vegetable.

4. The method of claim 1, wherein $R^1$ represents a hydrocarbon group that is a saturated aliphatic hydrocarbon group.

5. The method of claim 4, wherein the saturated aliphatic hydrocarbon group is selected from the group consisting of methyl, ethyl, n-propyl, isopropyl, n-butyl, isobutyl, tert-butyl, n-pentyl and n-hexyl.

6. The method of claim 1, wherein the plant is selected from the group consisting of barley, Komatsuna turnip green, garland chrysanthemum, broccoli and radish.

7. The method of claim 1, wherein the composition further comprises a plant growth modifier, a saccharide, a nitrogen containing compound, an acid, an alcohol, a vitamin, a trace element, a metal salt, a chelating agent, a preservative or an antifungal agent.

8. The method of claim 1, comprising applying 0.005 ppm to 1 ppm of the 5-amino-4-hydroxypentanoic acid, or a salt thereof.

* * * * *